United States Patent
Claus et al.

(10) Patent No.: US 7,921,017 B2
(45) Date of Patent: Apr. 5, 2011

(54) SYSTEMS AND METHODS FOR VOICE CONTROL OF A MEDICAL DEVICE

(75) Inventors: Michael J. Claus, Newport Coast, CA (US); James W. Staggs, Laguna Niguel, CA (US)

(73) Assignee: Abbott Medical Optics Inc, Santa Ana, CA (US)

( * ) Notice: Subject to any disclaimer, the term of this patent is extended or adjusted under 35 U.S.C. 154(b) by 992 days.

(21) Appl. No.: 11/490,846

(22) Filed: Jul. 20, 2006

(65) Prior Publication Data

US 2008/0021711 A1 Jan. 24, 2008

(51) Int. Cl.
*G10L 15/00* (2006.01)
*G10L 15/04* (2006.01)
*G10L 21/00* (2006.01)

(52) U.S. Cl. .......................... 704/275; 704/231; 704/253

(58) Field of Classification Search .................. None
See application file for complete search history.

(56) References Cited

U.S. PATENT DOCUMENTS

| | | | |
|---|---|---|---|
| 4,983,901 A | 1/1991 | Lehmer | |
| 5,268,624 A | 12/1993 | Zanger | |
| 5,345,538 A * | 9/1994 | Narayannan et al. | 704/275 |
| 5,970,457 A | 10/1999 | Brant et al. | |
| 6,278,975 B1 * | 8/2001 | Brant et al. | 704/275 |
| 6,295,391 B1 * | 9/2001 | Rudd et al. | 382/313 |
| 7,286,992 B2 * | 10/2007 | Sander et al. | 704/275 |
| 2001/0047263 A1 * | 11/2001 | Smith et al. | 704/275 |
| 2004/0068300 A1 | 4/2004 | Kadziauskas et al. | |
| 2005/0075545 A1 | 4/2005 | Honda et al. | |
| 2005/0242919 A1 | 11/2005 | Wang et al. | |
| 2006/0114175 A1 * | 6/2006 | Boukhny | 345/24 |
| 2006/0149301 A1 | 7/2006 | Claus | |
| 2006/0224107 A1 | 10/2006 | Claus et al. | |
| 2006/0224143 A1 | 10/2006 | Claus et al. | |

OTHER PUBLICATIONS

Anonymous: "Windows XP Speech Recognition"; Internet Article,[Online] XP002495590 Retrieved from teh internet: URL:http://www.chat11.com/Commands_In_Voice_Command_Mode> [retrieved on Sep. 12, 2008] the whole document.

* cited by examiner

*Primary Examiner* — David R Hudspeth
*Assistant Examiner* — Justin W Rider

(57) ABSTRACT

The invention is generally directed to systems and methods for medical care, and more particularly to systems and methods for voice control of a medical device. A first embodiment includes a voice controlled surgical system, such as a phacoemulsification system, a microphone coupled to the surgical system, and a voice controlled computer interface coupled with the surgical system. The voice controlled interface is configured to receive a request to invoke a voice command via the microphone, to listen for a voice command upon receipt of a valid request to invoke a voice command, and to forward a valid voice command upon receipt of the valid voice command to the surgical system for execution.

24 Claims, 4 Drawing Sheets

SYSTEMS AND METHODS FOR VOICE CONTROL OF A MEDICAL DEVICE

FIELD OF THE INVENTION

The field of the invention relates to systems and methods for medical care, and more particularly to systems and methods for voice control of a medical device.

BACKGROUND OF THE INVENTION

Surgical systems, such as phacoemulsification systems for ophthalmic surgery, typically involve complex user interfaces that require one or both hands to manipulate. However, the primary user of such systems, the surgeon, typically has his/her hands fully occupied with the actual surgical procedure. In addition, the surgeon is typically located in a sterile field, and the surgical equipment may not be within the field. Thus, changes to the settings and configuration of the surgical equipment by the surgeon would require the surgeon to break the sterile field, use an indirect mechanism to interact with the equipment's user interface, or ask another person present in the operating room (such as a nurse) to make changes on his/her behalf.

To address this issue, equipment manufacturers have developed foot pedal interfaces that allow the surgeon to utilize his/her feet to manipulate the device. However, on medical systems with large numbers of configurations and settings, the foot pedal interface can become large, expensive and confusing to the user. One such complicated medical system known in the art is a phacoemulsification system, which removes the lens of an eye damaged by cataract. Turning to FIG. 1, a functional block diagram of a phacoemulsification system known in the art is shown. The system 100 may include a control unit 102 and a handpiece 104 operably coupled together. As shown in FIG. 2, the handpiece 104 may include a needle 106 for insertion into an eye E and a vibrating unit 108 that is configured to ultrasonically vibrate the needle 106. The vibrating unit 108, which may include, e.g., a piezoelectric crystal, vibrates the needle 106 according to one or more parameters, such as frequency, pulse width, shape, size, duty cycle, amplitude, and so on.

The phacoemulsification system 100 includes a microprocessor computer 110 which is operably connected to and controls the various other elements of the system. In a number of embodiments, the system 100 may include a variable speed pump 112, which can be a peristaltic and/or venture pump known in the art, for providing a vacuum source and a pulsed ultrasonic power source 114 for providing control outputs to a pump speed controller 116 and an ultrasonic power level controller 118. A vacuum sensor 120 provides an input to the computer 110 representing the vacuum level on the output side of the pump 112. Venting may be provided by a vent 122. The system 100 may also include a phase detector 124 for providing an input to the computer 100 that represents a phase shift between a sine wave representation of the voltage applied to the handpiece 104 and the resultant current into the handpiece 104. The functional representation of the system 100 also includes a system bus 126 to enable the various elements to be operably in communication with each other.

In operation, the control unit 102 supplies ultrasonic power to the phacoemulsification handpiece 104. An irrigation fluid source 128 provides irrigation fluid to the handpiece 104. The irrigation fluid and an ultrasonic pulse are applied by the handpiece 104 to a patient's eye E, which are indicated by arrows F and P, respectively. Aspiration of the eye E is achieved by means of the pump 112, which is indicated by arrow A.4 The handpiece 104 may include a switch 130 for enabling a surgeon to select an amplitude of electrical pulses to the handpiece 104 via the computer 110, the power level controller 118, and the ultrasonic power source 114. The operation of the system 100 in general may be in accordance with the disclosure of U.S. Pat. No. 6,629,948, which is incorporated herein in its entirety by reference.

As shown above, there are many parameters of the system 100 controllable by the surgeon associated with the various functions described above, e.g., rate of aspiration, rate of irrigation, and ultrasonic power level. These parameters can be controllable by various interfaces, such as computer user interfaces and/or foot pedals/switches. An example computer user interface for system 100 is described in U.S. patent application Ser. No. 11/030,443 entitled "Phacoemulsification System Utilizing Graphical User Interfaces for Adjusting Pulse Parameters," and an example foot pedal/switch control is described in U.S. Pat. No. 4,983,901 entitled "Digital Electronic Foot Control for Medical Apparatus and the Like" and U.S. Pat. No. 5,268,624 entitled "Footpedal Control with User Selectable Operational Ranges." All three of these references are herein incorporated by reference in their entirety into the present application. As mentioned above, these interfaces can become large, expensive, and confusing to the user.

One approach to simplify the interface(s) is to incorporate a voice controlled interface, wherein the surgeon can simply voice a command to control the various parameters; however, existing voice command interfaces require the operator to provide an additional confirmation command after the original voice command. For example, after an operator vocally requests setting ultrasonic power level, the system 100 generates a confirmation as to what the system 100 recognizes the operator's request to be, e.g., a computer message identifying the recognized command. Subsequently, the operator is then required to provide an additional vocal "yes" or "no" to confirm the request. An example of such a system is described in U.S. Pat. No. 5,970,457, which is herein incorporated by references in its entirety. One concern about this approach is that it may cause an undesirable delay in operation. Accordingly, an improved voice controlled interface is desirable.

SUMMARY OF THE INVENTION

The invention is generally directed to systems and methods for medical care, and more particularly to systems and methods for voice control of a medical device. A first embodiment includes a voice controlled surgical system, such as a phacoemulsification system, a microphone coupled to the surgical system, and a voice controlled computer interface coupled with the surgical system. The voice controlled interface is configured to receive a request to invoke a voice command via the microphone, to listen for a voice command upon receipt of a valid request to invoke a voice command, and to forward a valid voice command upon receipt of the valid voice command to the surgical system for execution.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

In order to better appreciate how the above-recited and other advantages and objects of the inventions are obtained, a more particular description of the embodiments briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

DETAILED DESCRIPTION OF THE PREFERRED EMBODIMENTS

Figure 1:
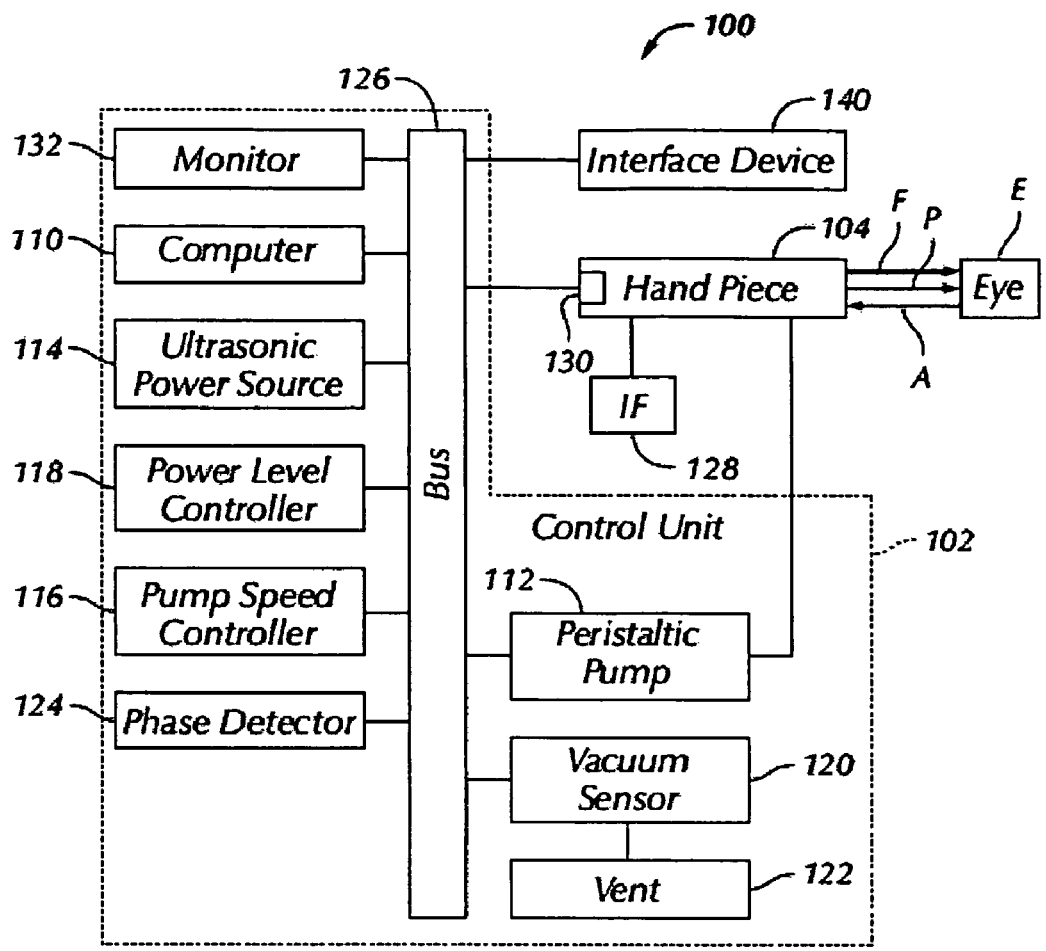
FIG. 1 shows a diagram of a phacoemulsification system known in the art.
Figure 2:
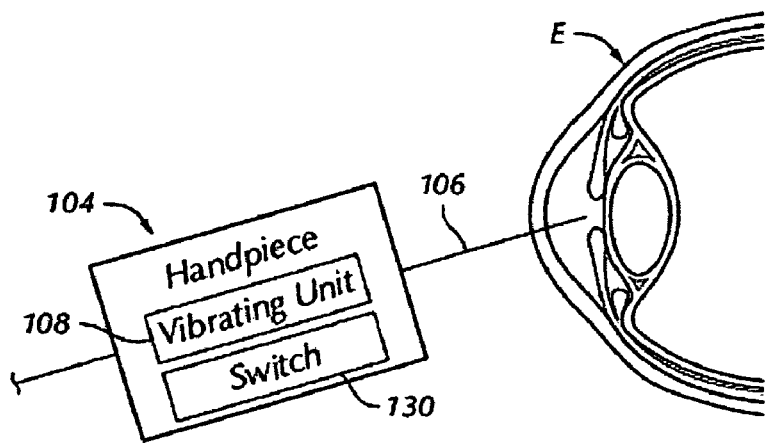
FIG. 2 shows a handpiece for a phacoemulsficiation system known in the art.
Figure 3:
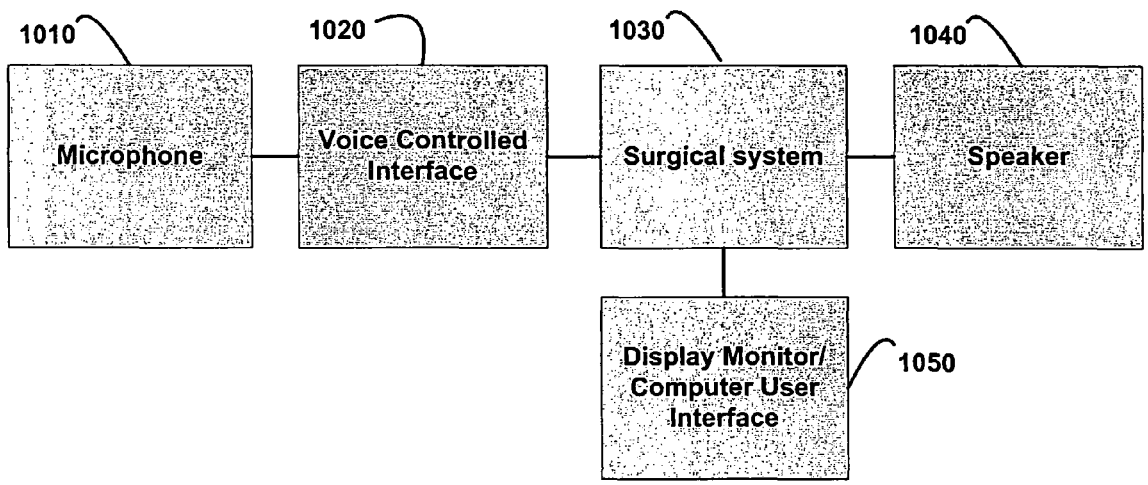
FIG. 3 shows a surgical system with a voice controlled interface in accordance with a preferred embodiment of the present invention.

As mentioned above, voice controlled surgical systems are known in the art; however, existing voice command interfaces require the operator to provide an additional confirmation command after the original voice command, which can cause undesirable delays during time sensitive operations. A system 1000 having a voice controlled interface 1020 coupled with a surgical system 1030, such as a phacoemulsification system shown in FIG. 1, is shown in FIG. 3. The system 1000 further includes a microphone 1010 coupled to the voice controlled interface 1020 to receive audio signals, a speaker coupled to the surgical system 1030 for audio output 1040 and a display monitor 1050 coupled to the surgical system 1030 to provide a computer user interface. The computer user interface can be a graphical user interface. Alternatively, the computer user interface can be provided by a separate computing system, such as a personal computer (not shown), in communication with the surgical system 1030.

The voice controlled interface 1020 can be implemented as a hardware and/or software component coupled with or integrated with the surgical system. The interface 1020 includes a speech recognition module, such as, for example, the VR Stamp™ from Sensory available in the commercial market. The interface 1020 can preferably be used without the need to train the speech recognition module to a particular user's voice and can preferably recognize more than one language. However, if the interface 1020 is trained for a particular operator's voice, for example, a particular surgeon, then the data associated with the training may be kept with the operator's profile in a database, which one of ordinary skill in the art would appreciate.

Figure 4:
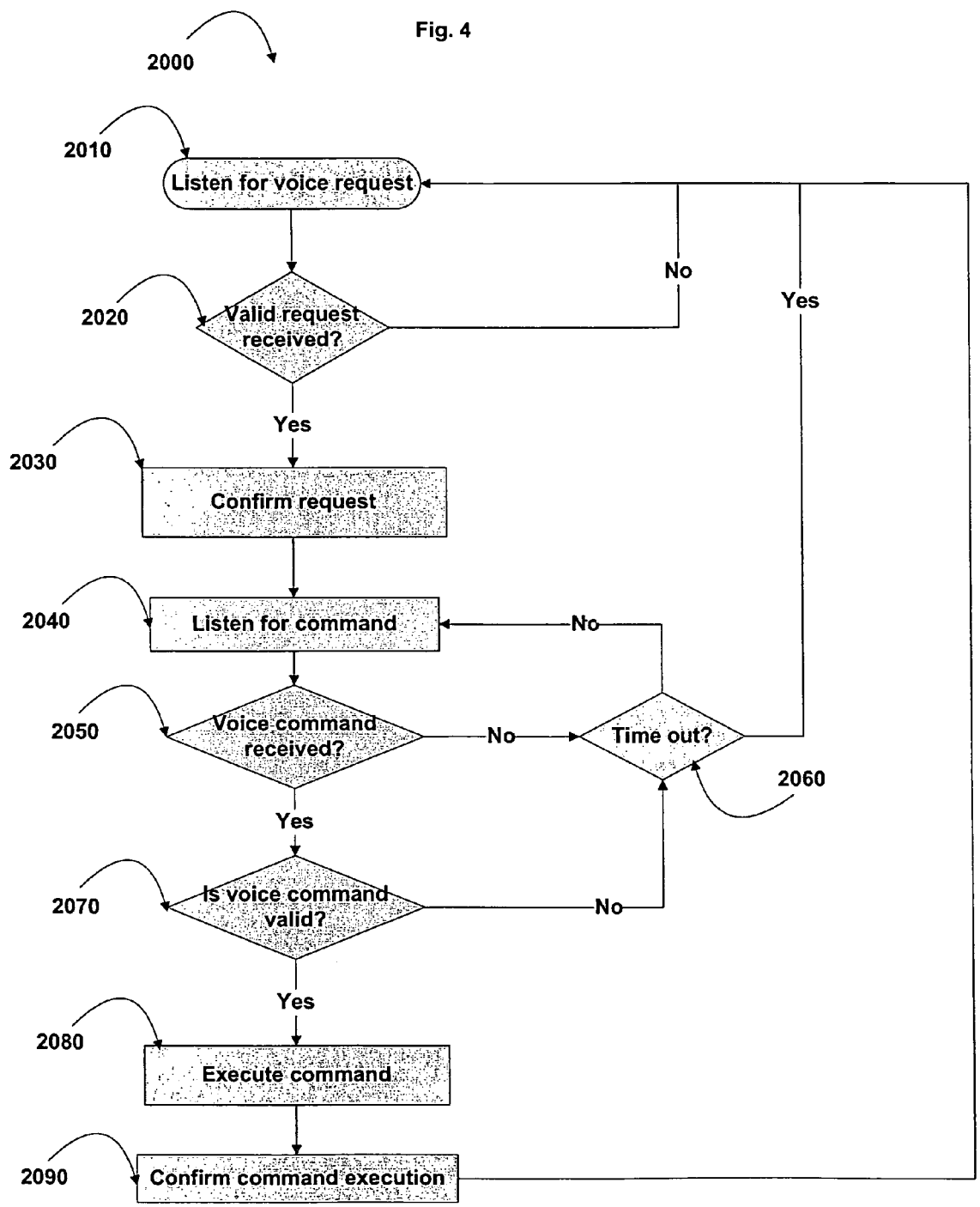
FIG. 4 shows a flow diagram of the operation of a voice controlled interface in accordance with a preferred embodiment of the present invention.

Turning to FIG. 4, a flow diagram 2000 illustrating the operation of the voice controlled interface 1020 is shown. The interface 1020 first listens for a request to invoke a voice command (configurable by the operator) (start block 2010), which causes the interface 1020 to listen for a voice command, such as "adjust power level." The request can come from the operator by any recognizable means, such as a unique vocal keyword (configurable by the operator) that will preferably not be accidentally voiced during operation, e.g., "A-M-O." The request for a voice command can further originate from a touch screen display monitor 1050, a foot pedal (not shown), or any other peripheral interface operably coupled to the surgical system 1030. Moreover, the request for a voice command may require a continuous input while issuing a voice command, e.g., require that the foot pedal be continuously depressed at a certain position.

Upon receipt of a valid request for a voice command, the interface 1020 will generate a confirmation to notify the operator that a request for a voice command was recognized and that the interface 1020 is waiting for a voice command (decision block 2020) and (action block 2030). The confirmation can be audible, e.g., a beep, and/or visual, e.g., a notification on the display monitor 1050. After confirmation (action block 2030), the interface 1020 will then listen for a voice command (action block 2040) associated with a function of the surgical system 1030, e.g., in the case of a phacoemulsification system 100, aspiration rate, irrigation rate, phaco power level, etc . . . Other examples will be described below.

The interface 1020 can be configured to wait a finite time period to receive a valid voice command after a valid request for a voice command has been received and confirmed. If a voice command has not yet been received (decision block 2050), then the interface 1020 will determine whether the finite time period has lapsed (decision block 2060), and if so, then the interface 1020 will wait/listen for another request for a voice command (start block 2010). If the finite time period has not lapsed, then the interface 1020 will continue to wait for a voice command (action block 2040). Upon receipt of a voice command, the interface 1020 will then determine whether the voice command is valid (decision block 2070). This determination can be made using a number of factors, including without limitation whether the voice of the received voice command matches the voice of the request for a voice command, whether the voice of the received voice command matches a valid operator's voice, and/or whether the received voice command matches an internal table of configured recognized voice commands. If no valid voice command has been received yet (decision block 2070), then the interface 1020 will determine whether the finite time period has lapsed (decision block 2060).

If a valid command has been received (decision block 2070), the interface 1020 will then interpret the valid voice command into a command recognizeable by the surgical system 1030, e.g., a computer readable data string, and forward the interpreted command to the surgical system 1030 for execution (action block 2080), and a confirmation of the executed command will be generated (action block 2090). This confirmation notifies the surgeon of the completed execution of the command, which can be in the form of an audio signal and/or visual signal. After confirmation of the executed command, the interface 1020 will then listen for another request for a voice command (start block 2010). An additional safety component can further be added, which determines whether the received voice command conflicts with a command from another input device, such as the foot pedal (not shown). For example, a voice command may be associated with the increase of power; however the foot pedal is set at a position for decreasing power. The interface 1020 can be configured to have either one interface or the other take priority, or have both interfaces fail and an alert generated notifying the operator.

The approach described above circumvents the need for a subsequent confirmation by the operator after the operator has submitted a voice command, which will substantially reduce delays during operation compared to prior existing voice interfaces. These prior voice interfaces require the subsequent confirmation because the prior interfaces cannot distinguish between a valid voice command or incidental noise near the microphone that is similar to a valid voice command. This is partly due to the fact that the prior interfaces have to be prepared to receive a voice command at any time. In the system 1000 described above; however, the interface 1020 will not listen for a voice command until a valid request for a voice command is received. Thus, the interface 1020 can expect the next voice signal received to be a valid voice command. In this approach, request for a voice command, voice command, and all other incidental noise can be readily distinguishable by the interface 1020, and the system 1000 can execute the voice command without further confirmation.

In the case of a phacoemulsification surgical system, the following is a sample list of parameters that can be configured to be associated with voice commands recognizeable by a voice control interface 1020 in accordance with a preferred embodiment:

"Phaco <XX>" where XX is an integer between 1 and 4: While the phacoemulsification system is in a mode to perform the actual phacoemulsification procedure, known as "phaco mode," the surgeon may have different settings for different situations depending on, for example, hardness of cataract, stage of procedure, etc . . . The different settings, e.g., ultrasonic power, irrigation rate, etc . . . , may be stored in different modes, which can be labeled by numbers, e.g., 1 thru 4, which thus can be invoked by voice command.

"IA <XX>" where XX is an integer between 1 and 3: The different irrigation and aspiration settings ("IA") can be stored and preset in different modes, which also can be labeled by numbers, e.g., 1 thru 3, and invoked by voice command.

"Diathermy <XX>" where XX is an integer between 1 and 2: Diathermy is a mode of operation in which a surgeon can cauterize any bleeding wounds, and again, involves various settings known in the art which can be preset and stored by modes, labeled by numbers and invoked by voice command.

"Vitrectomy <XX>" where XX is an integer between 1 and 2: This mode of operation for the phacoemulsification system relates to cutting the vitreous of the eye, and also involves various settings stored by different modes.

"Light <XX>" where XX is an integer between 0 and 10: This command allows for different light settings, e.g., intensity of light.

"Bottle <XX>" where XX is an integer between 0 and 107, "Bottle Up", "Bottle Down", and "Bottle Height": All are commands that control irrigation bottle height, in units, e.g., inches, or percentage, which controls irrigation flow and pressure.

"CASE <XX>" where XX is an integer between −2 and +2: The various settings related to the fluidics of the phasoemulsification system can be stored in different modes controllable by voice command. "CASE" and fluidics control are described in U.S. patent application Ser. No. 11/401,529, entitled "APPLICATION OF A SYSTEM PARAMETER AS A METHOD AND MECHANISM FOR CONTROLLING EYE CHAMBER STABILITY" and U.S. patent application Ser. No. 11/086,508, entitled "APPLICATION OF VACUUM AS A METHOD AND MECHANISM FOR CONTROLLING EYE CHAMBER STABILITY", both of which are herein incorporated by reference in their entirety.

"Vacuum <XX>" where XX is an integer between 0 and 650, and "Max Vac": These commands control vacuum settings.

"Flow <XX>" where XX is an integer between 0 and 60, and "Max Flow": These commands control flow settings.

"Power <XX>" where XX is an integer between 0 and 100, and "Max Power": These commands control ultrasonic power settings, which can be preset and stored in different modes. In addition, if the power is emitted in pulses, than the rate or the duty cycle of the pulses can be controlled by voice command. A description of the control of duty cycles of pulse emitted ultrasonic power is described in U.S. patent application Ser. No. 10/680,595, entitled "CONTROL OF PULSE DUTY CYCLE BASED UPON FOOTSWITCH DISPLACEMENT," which is hereby incorporated by reference in its entirety. Settings related to the power and the duty cycles can be controlled directly or through modes such as those described above.

Other features that can be controlled by the voice interface 1020 include a dictation system (not shown) which records narration and commands provided by operator; the video monitor 1050 screen, wherein, e.g., the application windows in the screen can be switched by voice command; and a video recording system (not shown).

For phacoemulsification systems that include multiple pumps, e.g., a peristaltic and/or a venturi pump known in the art, the voice control interface 1020 can also be utilized to switch between the various pumps.

Figure 5:
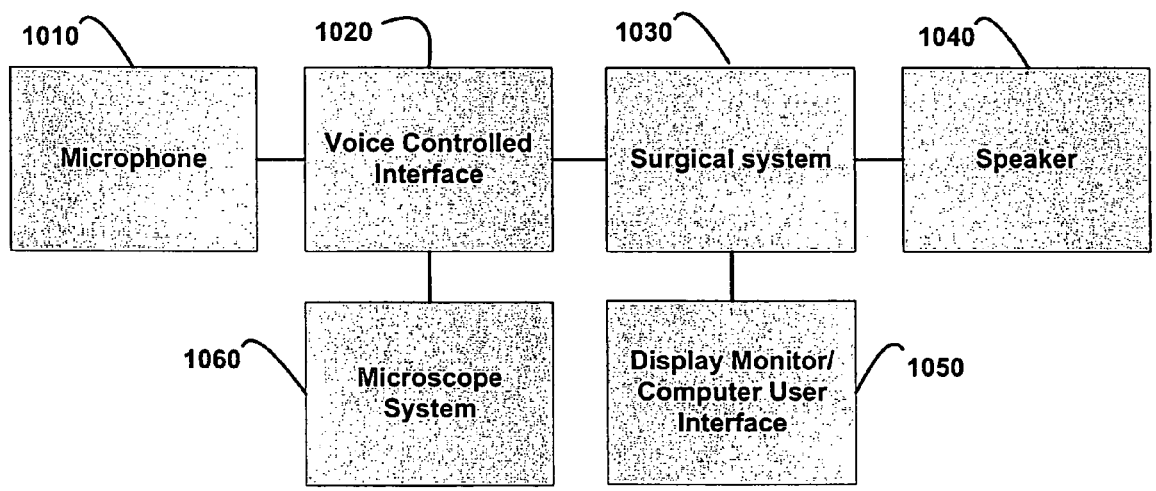
FIG. 5 shows an alternative surgical system with a voice controlled interface in accordance with a preferred embodiment of the present invention.

Turning to FIG. 5, a computer controllable microscope system 1060 can be coupled with the voice controlled interface 1020. The computer controllable microscope 1060 can include a processor for controlling features of the microscope such as auto focus and zoom (not shown), which then can be coupled to one or more mechanical servos or actuators for mechanically controlling such features. In the alternative, computer and servo/actuator components can be added to a manually controlled microscope (not shown), as one of ordinary skill in the art would appreciate. The voice controlled interface 1020 coupled to the microscope system 1060 can then enable an operator to vocally command the features of the microscope such as zoom and focus.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, and the invention may appropriately be performed using different or additional process actions, or a different combination or ordering of process actions. For example, this invention is particularly suited for applications involving medical systems, but can be used beyond medical systems in general. As a further example, each feature of one embodiment can be mixed and matched with other features shown in other embodiments. Additionally and obviously, features may be added or subtracted as desired. Accordingly, the invention is not to be restricted except in light of the attached claims and their equivalents.

What is claimed is:

1. A voice controlled surgical system comprising:
    a surgical system;
    a microphone coupled to the surgical system; and
    a voice controlled computer interface coupled with the surgical system configured to receive a request to invoke a voice command via the microphone, the request to invoke the voice command recognizable by the voice controlled computer interface as one of a set of predetermined allowable requests to invoke voice commands, wherein the voice controlled computer interface, upon recognition of the request to invoke the voice command as one of the set of predetermined allowable requests to invoke voice commands and without further confirmation, is configured to listen for a voice command for a predetermined period of time, and to interpret a valid voice command into a command recognizable by the surgical system upon receipt of the valid voice command within the predetermined period of time, and to forward the command recognizable by the surgical system to the surgical system for execution.

2. The system of claim 1, wherein the surgical system is a phacoemulsification system.

3. The system of claim 1, wherein the request to invoke a voice command is a vocal request.

4. The system of claim 1, further comprising a foot pedal coupled with the surgical system, wherein the foot pedal includes a switch configured to invoke a request to invoke a voice command.

5. The system of claim 1, further comprising a peripheral device coupled to the surgical system configured to invoke a request to invoke a voice command.

6. The system of claim 1, wherein the voice controlled surgical system is configured to generate a confirmation signal upon receipt of a valid request to invoke a voice command, wherein the confirmation is in the form of an audio signal or a visual signal.

7. The system of claim 1, wherein the voice controlled surgical system is configured to generate a confirmation signal upon receipt of a valid voice command, wherein the confirmation is in the form of an audio signal or a visual signal.

8. The system of claim 1, wherein the voice controlled computer interface coupled with the surgical system is further configured to determine whether the voice command conflicts with a command from a device after interpreting a valid voice command into a command recognizable by the surgical system upon receipt of the valid voice command within the predetermined period of time.

9. A computer program product that includes a non-transitory computer-usable medium having a sequence of instructions which, when executed by a processor, causes said processor to execute a process for providing a voice controlled interface coupled to a surgical system, said process comprising:
   receiving a request to invoke a voice command associated with a function of the surgical system, the request to invoke the voice command recognizable as one of a set of predetermined allowable requests to invoke voice commands;
   upon recognition of the request to invoke the voice command as one of the set of predetermined allowable requests to invoke voice commands and without further confirmation, listening for a voice command for a predetermined period of time;
   interpreting a valid voice command into a command recognizable by the surgical system upon receipt of the valid voice command within the predetermined period of time; and
   forwarding the command recognizable by the surgical system to the surgical system for execution.

10. The computer program product of claim 9, wherein the surgical system is a phacoemulsification system.

11. The computer program product of claim 9, wherein the request to invoke a voice command is a vocal request.

12. The computer program product of claim 9, wherein the request to invoke a voice command comes from a foot pedal coupled to the surgical system.

13. The computer program product of claim 9, wherein the request to invoke a voice command comes from a computer peripheral device coupled to the surgical system.

14. The computer program product of claim 9, wherein the computer program product is configured to generate a confirmation signal upon receipt of a valid request to invoke a voice command, wherein the confirmation is in the form of an audio signal or a visual signal.

15. The computer program product of claim 9, wherein the computer program product is configured to generate a confirmation signal upon receipt of a valid voice command, wherein the confirmation is in the form of an audio signal or a visual signal.

16. The computer program product of claim 9, wherein after interpreting a valid voice command into a command recognizable by the surgical system upon receipt of the valid voice command within the predetermined period of time, determining whether the voice command conflicts with a command from a device.

17. A method for processing a voice command, comprising:
   providing a voice controlled computer interface coupled to a surgical system;
   receiving a request to invoke a voice command associated with a function of the surgical system the request to invoke the voice command recognizable as one of a set of predetermined allowable requests to invoke voice commands;
   upon recognition of the request to invoke the voice command as one of the set of predetermined allowable requests to invoke voice commands and without further confirmation, listening for a voice command upon receipt of a valid request to invoke a voice command for a predetermined period of time;
   interpreting a valid voice command into a command recognizable by the surgical system upon receipt of the valid voice command within the predetermined period of time; and
   forwarding the command recognizable by the surgical system to the surgical system for execution,
   wherein the receiving, listening, interpreting, and forwarding is performed via the voice controlled computer interface.

18. The method of claim 17, wherein the surgical system is a phacoemulsification system.

19. The method of claim 17, wherein the request to invoke a voice command is a vocal request.

20. The method of claim 17, wherein the request to invoke a voice command comes from a foot pedal coupled to the surgical system.

21. The method of claim 17, wherein the request to invoke a voice command comes from a computer peripheral device coupled to the surgical system.

22. The method of claim 17, further comprising generating a confirmation signal upon receipt of a valid request to invoke a voice command, wherein the confirmation is in the form of an audio signal or a visual signal.

23. The method of claim 17, further comprising generating a confirmation signal upon receipt of a valid voice command, wherein the confirmation is in the form of an audio signal or a visual signal.

24. The method of claim 17, wherein after interpreting a valid voice command into a command recognizable by the surgical system upon receipt of the valid voice command within the predetermined period of time, determining whether the voice command conflicts with a command from a device.

* * * * *